(12) United States Patent
Zhang et al.

(10) Patent No.: US 9,453,937 B2
(45) Date of Patent: Sep. 27, 2016

(54) STATIONARY CT APPARATUS

(71) Applicant: Nuctech Company Limited, Beijing (CN)

(72) Inventors: Jinyu Zhang, Beijing (CN); Bin Sang, Beijing (CN); Zhanjun Duan, Beijing (CN); Li Zhang, Beijing (CN); Ziran Zhao, Beijing (CN)

(73) Assignee: Nuctech Company Limited, Beijing (CN)

( * ) Notice: Subject to any disclaimer, the term of this patent is extended or adjusted under 35 U.S.C. 154(b) by 408 days.

(21) Appl. No.: 14/140,058

(22) Filed: Dec. 24, 2013

(65) Prior Publication Data

US 2014/0185743 A1 Jul. 3, 2014

(30) Foreign Application Priority Data

Dec. 27, 2012 (CN) .......................... 2012 1 0581446

(51) Int. Cl.
  *G01V 5/00* (2006.01)
  *G01N 23/04* (2006.01)
  *G01T 1/29* (2006.01)

(52) U.S. Cl.
  CPC .............. *G01V 5/005* (2013.01); *G01N 23/046* (2013.01); *G01T 1/2985* (2013.01); *G01N 2223/20* (2013.01); *G01N 2223/419* (2013.01); *G01N 2223/5015* (2013.01)

(58) Field of Classification Search
  CPC ...................... G01N 2223/419; G01N 23/046; G01V 5/005; A61B 6/032; A61B 6/4007; A61B 6/4014; A61B 6/4266
  See application file for complete search history.

(56) References Cited

U.S. PATENT DOCUMENTS

| 6,018,562 | A  | * | 1/2000 | Willson | G01N 23/087 378/57 |
| 2005/0078861 | A1 | * | 4/2005 | Usikov  | G06T 11/006 378/21 |
| 2005/0111610 | A1 | * | 5/2005 | De Man  | A61B 6/032 378/10 |
| 2006/0008047 | A1 | * | 1/2006 | Zhou    | A61B 6/032 378/10 |
| 2009/0123051 | A1 | * | 5/2009 | Tamai   | A61B 6/4233 382/132 |
| 2012/0033784 | A1 | * | 2/2012 | Matsuda | A61B 6/00 378/19 |

OTHER PUBLICATIONS

ChinaTungsten Online, "What is tungsten alloy?", (Oct. 3, 2012), from the Internet: <<https://web.archive.org/web/20121003230845/http://www.tungsten-alloy.com/>>.*

* cited by examiner

*Primary Examiner* — Glen Kao
(74) *Attorney, Agent, or Firm* — Christensen Fonder P.A.

(57) ABSTRACT

A stationary CT apparatus and a method of controlling the same. The stationary CT apparatus includes: a scanning passage; a stationary carbon nanotube X-ray source arranged around the scanning passage and comprising a plurality of ray emission focal spots; and a plurality of stationary detector modules arranged around the scanning passage and disposed opposite the X-ray source. At least some of the plurality of detector modules are arranged in a substantially L shape or a substantially Π shape when viewed in a plane intersecting the scanning passage. Reconstruction of the CT apparatus without a rotary gantry is achieved and special substances in an object under inspection is identified by optimizing design of the carbon nanotube X-ray source and the detector device. The invention ensures that the stationary gantry type CT system has a small size and a high accuracy and is particularly suitable for safety inspection of baggage.

20 Claims, 3 Drawing Sheets

US 9,453,937 B2

STATIONARY CT APPARATUS

PRIORITY CLAIM

The present application claims priority to Chinese Patent Application No. 201210581446.9 filed on Dec. 27, 2012, which said application is incorporated by reference in its entirety herein.

BACKGROUND OF THE INVENTION

1. Field of the Invention

The present invention relates to a CT apparatus without a gantry and a method of controlling the CT apparatus, in which reconstruction of the CT apparatus without a rotary gantry is achieved and special substances in an object under inspection is identified by designing a carbon nanotube ray source and a detector device. The present invention is particularly suitable for a CT apparatus for safety inspection.

2. Description of the Related Art

In an existing gantry-less CT apparatus, an X-ray source with a plurality of ray emission focal spots generally adopt a circular ring-shaped structure or a surface-array detector is used. As a result, the gantry-less CT apparatus has a big volume, a large weight, and a high price.

SUMMARY OF THE INVENTION

Accordingly, an object of the present invention is to provide a CT apparatus, which adopts a carbon nanotube based X-ray source and a linear array detector structure, thereby reducing the size and cost of the CT apparatus.

In accordance with an aspect of the present invention, there is provided a CT apparatus, comprising: a scanning passage; a stationary X-ray source arranged around the scanning passage and comprising a plurality of ray emission focal spots; and a plurality of stationary detector modules arranged around the scanning passage and disposed opposite the X-ray source.

In accordance with an aspect of the present invention, at least some of the plurality of detector modules are arranged in a substantially L shape or a substantially Π shape when viewed in a plane intersecting the scanning passage.

In accordance with an aspect of the present invention, at least some of the plurality of ray emission focal spots of the X-ray source are arranged in a substantially L shape, Π shape, or straight line shape when viewed in a plane intersecting the scanning passage.

In accordance with an aspect of the present invention, the plane is substantially perpendicular to the scanning passage.

In accordance with an aspect of the present invention, each detector module has a ray receiving surface, and the ray receiving surfaces of the plurality of detector modules abut against one another end to end such that rays emitted from the plurality of ray emission focal spots cannot pass between the ray receiving surfaces.

In accordance with an aspect of the present invention, elongation lines of external sides of sectorial ray beams emitted from the two ray emission focal spots respectively arranged at an end and another end of the plurality of ray emission focal spots intersect at a point of intersection, and a line formed by connecting the point of intersection to a central point of the ray receiving surface of one of the detector modules is perpendicular to the ray receiving surface of the one of the detector modules, when viewed in a plane intersecting the scanning passage.

In accordance with an aspect of the present invention, the plurality of ray emission focal spots of the X-ray source are arranged in a straight line shape or in a row.

In accordance with an aspect of the present invention, the plurality of detector modules are arranged substantially in the shape of a spatial helix.

In accordance with an aspect of the present invention, the plurality of ray emission focal spots of the X-ray source are arranged substantially in the shape of a spatial helix.

In accordance with an aspect of the present invention, among the plurality of ray emission focal spots of the X-ray source and the plurality of detector modules, the corresponding ray emission focal spots and detector modules are arranged in the same plane, and the plane is substantially perpendicular to the scanning passage or the plane is inclined with respect to the scanning passage.

In accordance with an aspect of the present invention, each detector module can receive a ray beam from at least one of the plurality of ray emission focal spots of the X-ray source.

In accordance with an aspect of the present invention, the plurality of ray emission focal spots are arranged in at least one row in a direction in which an object under inspection enters and leaves the scanning passage.

In accordance with an aspect of the present invention, the plurality of detector modules are arranged in at least one row in a direction in which an object under inspection enters and leaves the scanning passage.

In accordance with an aspect of the present invention, the CT apparatus further comprises: a correction device disposed between the plurality of ray emission focal spots and the plurality of detector modules for controlling doses of ray beams from the ray emission focal spots.

In accordance with an aspect of the present invention, the correction device is a grid device made of W—Ni—Fe alloy.

In accordance with an aspect of the present invention, a distance between the correction device and ray receiving surfaces of the detector is at least five times as large as a distance between the correction device and the ray emission focal spots.

In accordance with an aspect of the present invention, the X-ray source is a carbon nanotube X-ray source.

In accordance with an aspect of the present invention, the CT apparatus is a CT apparatus without a gantry.

In accordance with an aspect of the present invention, control of the plurality of ray emission focal spots of the X-ray source is achieved by a Controller Area Network (CAN) bus. The ray emission focal spots may be arranged at the same intervals over a length, and a sequence in which the ray emission focal spots emit rays may be arranged along a straight line or a curve.

The present invention can adopt a carbon nanotube X-ray source. By laying out the X-ray source and the detector reasonably, the present invention overcomes the disadvantages of the complicated structure and bulky volume of the conventional gantry-less CT apparatus, thereby achieving miniaturization of the CT apparatus, reducing its floor space, and improving availability of the CT apparatus.

DETAILED DESCRIPTION OF THE EMBODIMENTS

A further description of the invention will be made as below with reference to embodiments of the present invention taken in conjunction with the accompanying drawings.

Figure 5:
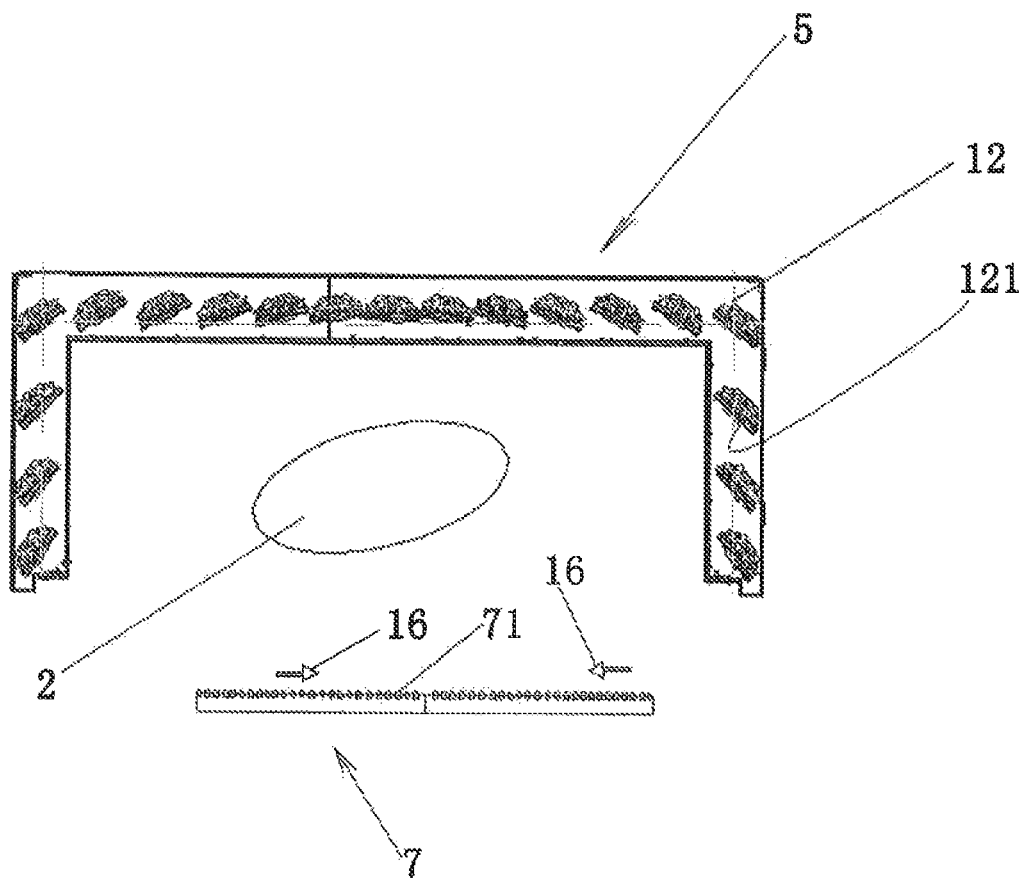
FIG. 5 is a schematic view showing layout of the ray source and the detector according to an embodiment of the present invention.

As shown in FIGS. 1-6, a CT apparatus 10 according to an embodiment of the present invention comprises: a scanning passage 4; a stationary X-ray source 7 including a plurality of ray emission focal spots 71; and a plurality of stationary detector modules 12 disposed opposite the X-ray source 7, and at least some of the detector modules 12 are arranged in a substantially L shape (FIGS. 2-4 and 6) or a substantially Π shape (FIG. 5) when viewed in a plane intersecting the scanning passage 4. The plane may be substantially perpendicular to the scanning passage 4 or a transfer direction of the transfer device 1, or at an angle with respect to the scanning passage 4 or the transfer direction of the transfer device 1. The plurality of ray emission focal spots 71 and the plurality of detector modules 12 are arranged around the scanning passage 4. The CT apparatus 10 may further comprise a detector arm 5 for fixing the detector modules 12, an acquisition control unit 6, a computer reconstruction unit 8, and the transfer device 1 for transferring an object 2 under inspection. The detector arm 5 may has a substantially L shape (FIGS. 2-4 and 6) or a substantially Π shape (FIG. 5). The plurality of ray emission focal spots 71 may be formed in an array by a single row of ray emission focal spots or a plurality of rows of ray emission focal spots. Alternatively, the detector modules 12 may also be arranged in any other shape such as a semicircular shape, a U shape, an arc shape, and a parabolic shape.

Figure 1:
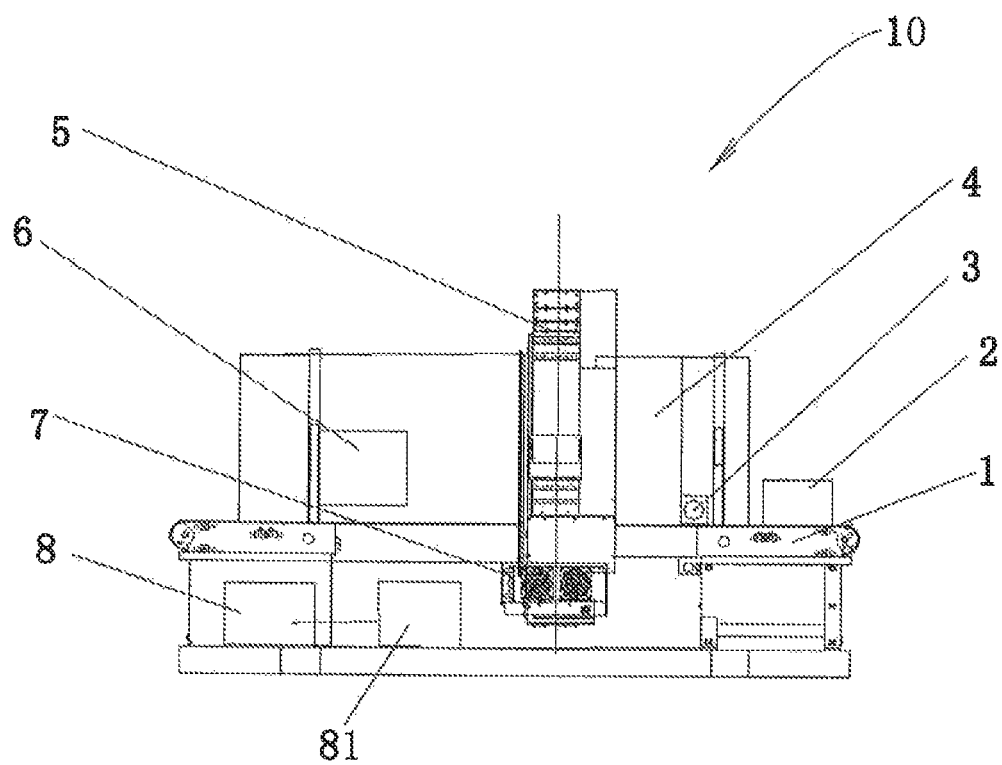
FIG. 1 is a schematic view of a CT apparatus according to an embodiment of the present invention.
Figure 2:
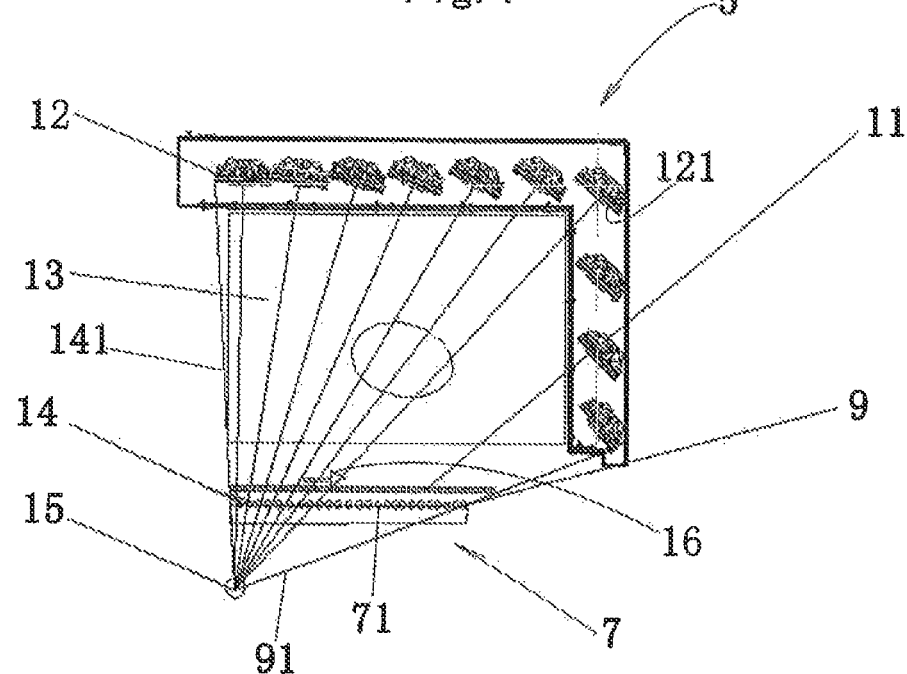
FIG. 2 is a schematic view showing layout of a ray source, a detector, and a correction device according to an embodiment of the present invention.

The X-ray source 7 may be a carbon nanotube X-ray source. At least some of the plurality of ray emission focal spots 71 of the X-ray source 7 are arranged in a substantially L shape (FIG. 3), Π shape, or straight line shape (FIGS. 2 and 4-6) when viewed in a plane intersecting the scanning passage. The plane may be substantially perpendicular to the scanning passage 4 or the transfer direction of the transfer device 1, or at an angle with respect to the scanning passage 4 or the transfer direction of the transfer device 1 and may be the above plane or different from the above plane. As shown in FIG. 2, a range covered by all of the sectorial X-ray beams emitted by the different ray emission focal spots 71 of the X-ray source 7 satisfies that an effective scanning area 13 in the scanning passage 4 can all be covered by the X-ray beams. Emission of the X-ray of each ray emission focal spot of the X-ray source is controlled by the acquisition control unit 6, and time when the X-ray emission focal spots 71 emit X-rays and an intensity of the X-ray are adjustable. In addition, the X-ray source 7 may also be any other appropriate X-ray source so long as it includes a plurality of controllable ray emission focal spots.

As shown in FIGS. 2-5, each detector module 12 has a ray receiving surface 121, and the ray receiving surfaces 121 of the plurality of detector modules 12 abut against one another end to end such that rays emitted from the plurality of ray emission focal spots 71 cannot pass between the ray receiving surfaces 121. On the detector arm 5, the detector modules 12 abut against one another end to end such that there is not a gap between the ray receiving surfaces and the ray receiving surfaces do not overlap one another in an orientation of the ray beams. The plurality of detector modules 12 may be arranged in a surface array or a linear array.

As shown in FIG. 2, the ray emission focal spots 71 are arranged in one row (which may be a curve-shaped row or an L-shaped row) or in a straight line when viewed in a plane intersecting the scanning passage 4, and elongation lines of external sides 91, 141 of the sectorial ray beams emitted from the ray emission focal spots 9 and 14 respectively arranged at an end and another end of the plurality of ray emission focal spots intersect at a point of intersection 15, and a line formed by connecting the point of intersection 15 to a central point of the ray receiving surface 121 of one of the detector modules 12 is perpendicular to the ray receiving surface 121 of the one of the detector modules 12, when viewed in the plane intersecting the scanning passage 4. The plane may be substantially perpendicular to the scanning passage 4 or the transfer direction of the transfer device 1, or at an angle with respect to the scanning passage 4 or the transfer direction of the transfer device 1.

The plurality of detector modules 12 may be arranged substantially in the shape of a spatial helix, and the plurality of ray emission focal spots of the X-ray source may also be arranged substantially in the shape of a spatial helix. Among the plurality of ray emission focal spots 71 of the X-ray source and the plurality of detector modules 12, the corresponding ray emission focal spots and detector modules may be arranged in the same plane. The plane may be substantially perpendicular to the scanning passage 4 or the transfer direction of the transfer device 1, or at an angle with respect to the scanning passage 4 or the transfer direction of the transfer device 1.

Each detector module 12 can receive a ray from at least one of the plurality of ray emission focal spots 71 of the X-ray source 7.

Figure 6:
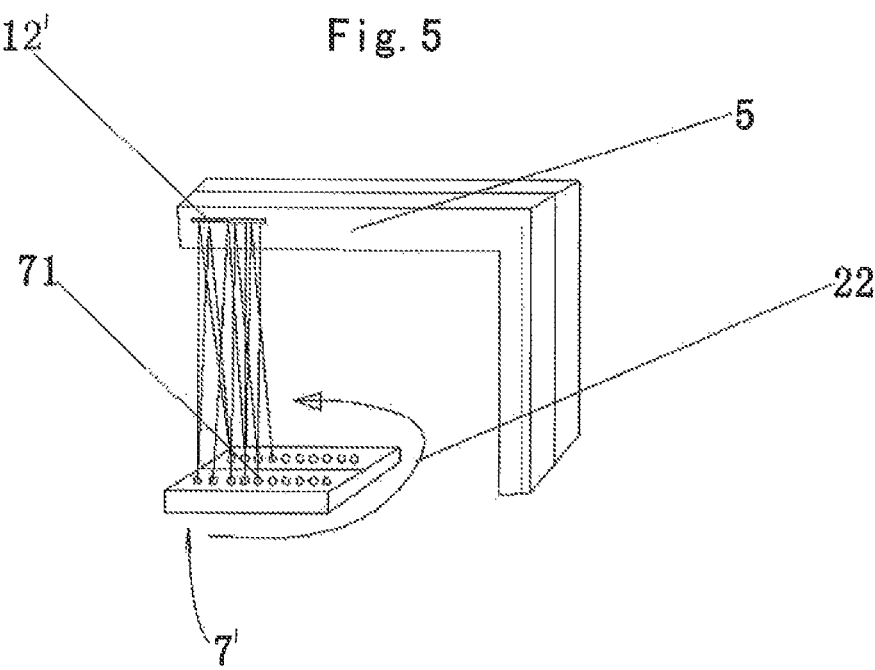
FIG. 6 is a schematic view showing layout of the ray source and the detector according to an embodiment of the present invention.

As shown in FIGS. 2-6, the ray emission focal spots 71 and the detector modules 12 are arranged in one plane when viewed in a plane intersecting the scanning passage 4, and the plane may be substantially perpendicular to the transfer direction of the transfer device 1, or at an angle with respect to the transfer direction of the transfer device 1. The plurality of ray emission focal spots 71 are arranged in one row and the plurality of detector modules 12 are arranged in at least one row in the transfer direction of the transfer device. As shown in FIG. 6, the plurality of ray emission focal spots 71 may be arranged in two or more rows, and the plurality of detector modules 12 may be arranged in two or more rows.

As shown in FIG. 2, the CT apparatus according to the present invention further comprises: a correction device 11 disposed between the plurality of ray emission focal spots 71 and the plurality of detector modules 12 for controlling doses of ray beams from the ray emission focal spots. The correction device 11 may be a correction grid. A distance between the correction grid and the ray receiving surfaces 121 of the detector 12 is at least five times as large as a distance between the correction grid and the ray emission focal spots 71.

Figure 3:
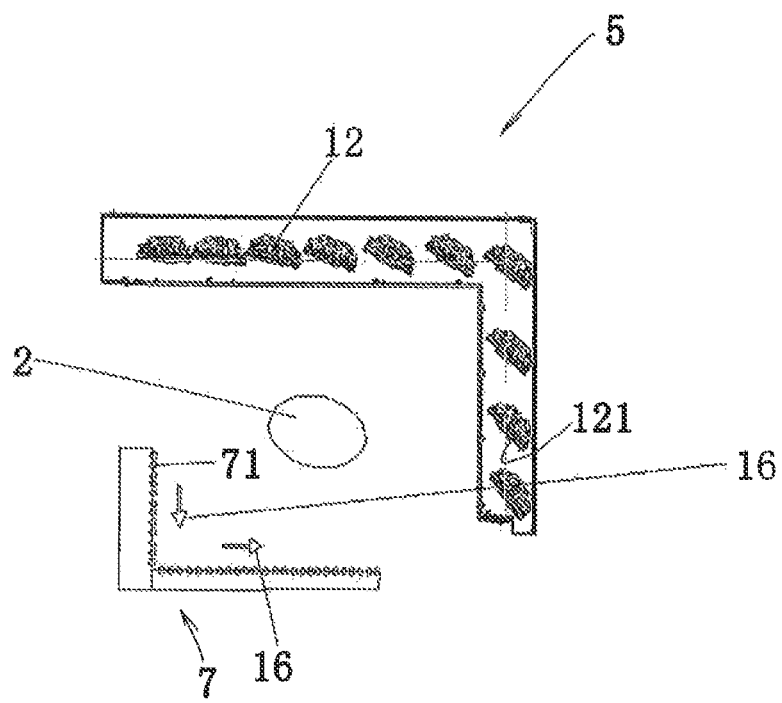
FIG. 3 is a schematic view showing layout of the ray source and the detector according to an embodiment of the present invention.
Figure 4:
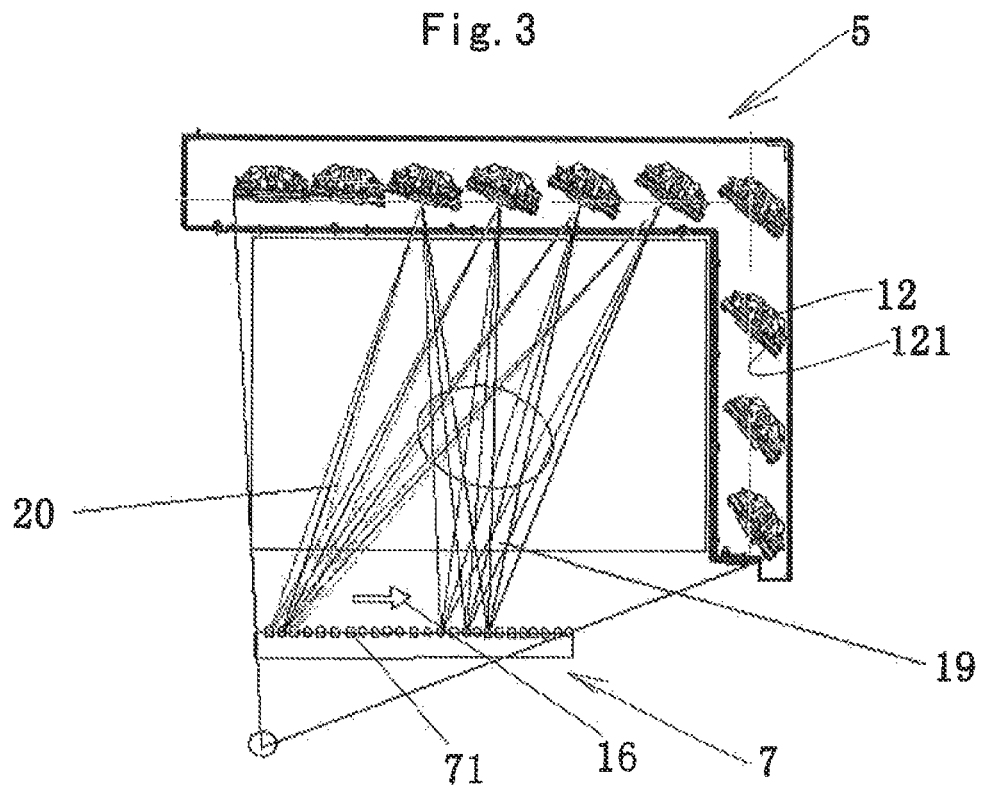
FIG. 4 is a schematic view showing layout of the ray source and the detector according to an embodiment of the present invention.

As shown in FIG. 3, in the CT apparatus with a stationary gantry in which the detector arm 5 has an L-shaped structure, or the detector modules 12 are arranged in an L shape, the ray emission focal spots 71 of the X-ray source 7 may also be arranged in an L shape.

In a period of time, X-ray energy reaching the ray receiving surfaces 121 of the detector 12 on the detector arm 5 may come from a single ray emission focal spot 71 of the X-ray source 7, or from a ray combination of several ray emission focal spots 71 of the X-ray source 7. The intensities of the X-rays emitted from the different ray emission focal spots 71 of the X-ray source 7 may be program-controllable. A number of the ray emission focal spots of the X-ray source 7 correlates with a size of the effective scanning area 13 within the scanning passage 4. The X-ray beams emitted from all of the ray emission focal spots 71 should cover the effective scanning area in the scanning passage 4.

A ray emitting manner of each X-ray emission focal spot 71 of the X-ray source 7 correlates with an acquisition control manner of the CT apparatus with a stationary gantry, and whether each ray emission focal spot 71 is triggered or not is controlled by the acquisition control unit 6 of the CT apparatus. The ray emission focal spots 71 of the X-ray source 7 may emit X-rays in sequence by instructions of the acquisition control unit 6, and the intervals and frequency at which the ray emission focal spots 71 emit the rays are controlled by the instructions of the acquisition control unit 6. The ray emission focal spots 71 of the X-ray source 7 may also emit X-rays at intervals or the ray emission focal spots 71 of the X-ray source 7 may also emit X-rays under program control.

A plane in which the detector arm 5 or the detector modules 12 and the ray emission focal spots 71 of the X-ray source 7 are located may be perpendicular to the scanning passage, the detector arm 5 or the detector modules 12 and the ray emission focal spots 71 of the X-ray source 7 may also be arranged in the shape of a spatial curve such as a spatial helix, and the detector modules 12 and the X-ray source 7 are arranged around the effective scanning area 13 of the scanning passage 4.

The plurality of detector module 12 are mounted to the detector arm 5, and may form an arc-shaped region around the scanning passage 4. A row or a plurality of rows of detector modules 12 may be mounted to each detector arm 5. The number of rows of the detector modules 12 on the detector arm 5 correlates with a scanning speed of the CT apparatus 10. The number of rows of the detector modules 12 may be less than or equal to 3 when the scanning speed is low (generally a moving speed of the transfer device 1 is less than 0.25 m/s), and the number of rows of the detector modules 12 may be greater than or equal to 5 or surface-array detector modules are used when the scanning speed is high (generally the moving speed of the transfer device 1 is larger than 0.3 m/s).

The detector modules 12 are mounted to the detector arm 5 and supported and fixed by the detector arm 5. A seal formed of a light-weight material is mounted at a portion, facing the X-ray source 7, of the detector arm 5 to block dust and foreign matter in the scanning passage 4 from entering the detector arm 5.

The linear array detector modules 12 or surface-array detector modules 12' may be mounted to the stationary detector arm 5. The number and distribution manner of the detector modules correlate with a length of the X-ray source 7 and distribution and orientation of the plurality of ray emission focal spots 71. The detector modules and the X-ray source 7 can ensure that the effective scanning area 13 in the scanning passage 4 is all covered by the X-ray beams.

In the CT apparatus 10 with a stationary gantry which has the X-ray source 7 with the plurality of ray emission focal spots 71, the acquisition control unit 6 performs control, including control of the X-ray source 7, control of the detector modules 12 and control of the computer reconstruction system, through a Controller Area Network (CAN) bus. The acquisition control unit 6 provides support for communication protocol, control redundancy, and emergency control. By parsing the instructions of the acquisition control unit 6, a control unit in the detector module 12 sends instructions for beginning data acquisition and transmits and error-corrects the acquired data, and the data acquired by the detector modules are transmitted to the computer reconstruction unit 8.

The computer reconstruction unit 8 is a key device for achieving parsing and reconstruction of the data and characteristic identification in the gantry-less CT apparatus. When the acquired data are transmitted to the computer reconstruction unit 8, the computer reconstruction unit 8 firstly classifies the data according to the formats of the data packages, determines the sources of the data, and establishes a characteristic matrix based on the baggage scanned in the scanning area, and then solves the characteristic matrix to find a corresponding characteristic value. By comparing the characteristic value with a characteristic value of special substance in a data bank, the computer reconstruction unit 8 judges whether the substance in the baggage is a substance to which special attention should be paid and further provides a prompt about whether an alarm is raised.

The function of the scanning passage 4 is to provide a passage in which the scanned baggage 2 is transferred and travels, and a shield wall for shielding irrelevant X-rays. The radiation shielding material is a heavy metal such as lead, steal or other materials.

During inspection, the baggage 2 under inspection is transferred into the scanning passage 4 at a speed by the belt of the transfer device 1. When the baggage 2 triggers a photoelectric sensor 3, the X-ray source 7 is brought into a state ready for emission. When the baggage 2 enters the effective scanning area 13, the acquisition control unit 6 controls the ray emission focal spots 71 of the X-ray source 7 to emit electronic beams so as to generate X-rays continuously or at intervals. Meanwhile, the acquisition control unit 6 sends instructions for beginning data acquisition so that the detector modules 12 at the corresponding positions begin acquiring data. At the same time, time when the data are acquired and the positions of the detector modules 12 that acquire the data are recorded. The acquired data are transmitted to the computer reconstruction unit 8 through a dedicated cable. The computer reconstruction unit 8 corrects energy values of the X-rays by comparing instruction information for controlling the ray emission focal spot and acquired data information which occur within the same moment with each other, and then the data at the corresponding position of the baggage are reconstructed to establish a matrix based on substance characteristic of the scanned baggage 2. The matrix is conversely solved by the computer reconstruction unit 8 to obtain a single or a plurality of substance characteristics of the scanned baggage 2 at the corresponding position and establish the substance characteristic data within a single slice position. As the baggage 2 moves at a speed, the computer reconstruction unit 8 will acquire the substance characteristic data of the entire baggage slice by slice. By a dedicated identification algorithm, the data characteristics of the slices are collectively analyzed and determined and compared with a substance characteristic table in an existing data bank, to obtain a conclusion about whether or not the baggage 2 under inspection contains a special substance concerned by a user and display an image of the baggage by a display 81 of the computer reconstruction unit 8.

In the present invention, the X-ray beams 19 and 20 emitted at different times are generated and data are acquired by switching among the ray emission focal spots and among scanning and acquiring areas by switching among the ray emission focal spots 71 of the X-ray source 7 which are located at respective positions. As a result, a computerized tomography scan of the baggage under inspection can be achieved by effectively utilizing the conventional computerized tomography (CT) technology without rotation of the object or rotation of the detector arm 5 and the X-ray source 7.

During reconstruction by the computer, an accuracy of the reconstruction of the tomography or slice data by the computer correlates with an angle at which the scanned baggage is observed. The present invention can adopt the X-ray source based on the carbon nanotube. Therefore, the ray emission focal spots may be arranged at the same intervals over a length. A sequence in which the ray emission focal spots emit rays may be arranged along a straight line (as shown by the arrows 16 in FIGS. 2-5) or a curve by program control performed by the acquisition control unit 6. A sequence in which the ray emission focal spots of the surface-array X-ray source 7' emit rays is arranged along a curve 22, and the curve 22 may be a spatial helix, and thus it is possible to improve a reconstruction accuracy of the system to the most degree.

The scanned baggage may pass through the scanning area at a speed, or may remain stationary within the scanning area until the scanning is completed. The computer system distinguishes substances by identifying the substance characteristics of the slices of the baggage. The substance characteristic is not limited to one type of characteristic, and may be a density and an atomic member.

The CT apparatus of the present invention can calculate and analyze the tomography or slice data at a higher rate, thereby providing an effective basis for a high-speed safety inspection CT system.

The invention claimed is:

1. A stationary CT apparatus, comprising:
    a scanning passage;
    a stationary X-ray source arranged partially around the scanning passage and comprising a plurality of ray emission focal spots; and
    a plurality of stationary detector modules arranged partially around the scanning passage and disposed opposite the X-ray source,
    elongation lines of external sides of sectorial ray beams emitted from two of the ray emission focal spots respectively arranged at one end and the other end of the plurality of ray emission focal spots intersect at a point of intersection, and a line formed by connecting the point of intersection to a central point of a ray receiving surface of each of the detector modules is perpendicular to the ray receiving surface of the each of the detector modules, when viewed in a plane intersecting the scanning passage,
    a first one of the two ray emission focal spots is arranged at the one end and a second one of the two ray emission focal spots is arranged at the other end;
    when viewed in the plane intersecting the scanning passage, the external side of the sectorial ray beam emitted from the first ray emission focal spot is located on one side that is away from the plurality of ray emission focal spots except the first ray emission focal spot, while the external side of the sectorial ray beam emitted from the second ray emission focal spot is located on the other side that is away from the plurality of ray emission focal spots except the second ray emission focal spot.

2. The stationary CT apparatus of claim 1, wherein
    at least some of the plurality of ray emission focal spots of the X-ray source are arranged in a substantially L shape, Π shape, or straight line shape when viewed in a plane intersecting the scanning passage.

3. The stationary CT apparatus of claim 2, wherein
    the plane is substantially perpendicular to the scanning passage or the plane is inclined with respect to the scanning passage.

4. The stationary CT apparatus of claim 2, wherein
    at least some of the plurality of detector modules are arranged in a substantially L shape or a substantially Π shape when viewed in a plane intersecting the scanning passage.

5. The stationary CT apparatus of claim 4, wherein
    the plurality of ray emission focal spots of the X-ray source are arranged in a straight line shape.

6. The stationary CT apparatus of claim 1, wherein
    the ray receiving surfaces of the plurality of detector modules abut against one another end to end such that rays emitted from the plurality of ray emission focal spots cannot pass between the ray receiving surfaces.

7. The stationary CT apparatus of claim 1, wherein
    at least some of the plurality of detector modules are arranged in a substantially L shape or a substantially Π shape when viewed in a plane intersecting the scanning passage.

8. The stationary CT apparatus of claim 7, wherein
    the plurality of ray emission focal spots of the X-ray source are arranged in a straight line shape.

9. The stationary CT apparatus of claim 7, wherein
    the plane is substantially perpendicular to the scanning passage or the plane is inclined with respect to the scanning passage.

10. The stationary CT apparatus of claim 1, wherein
    the plurality of detector modules are arranged substantially in the shape of a spatial helix.

11. The stationary CT apparatus of claim 1, wherein
    the plurality of ray emission focal spots of the X-ray source are arranged substantially in the shape of a spatial helix.

12. The stationary CT apparatus of claim 1, wherein
    among the plurality of ray emission focal spots of the X-ray source and the plurality of detector modules, the corresponding ray emission focal spots and detector modules are arranged in the same plane, and the plane is substantially perpendicular to the scanning passage or the plane is inclined with respect to the scanning passage.

13. The stationary CT apparatus of claim 1, wherein
    each detector module can receive a ray beam from at least one of the plurality of ray emission focal spots of the X-ray source.

14. The stationary CT apparatus of claim 1, wherein
    the plurality of ray emission focal spots are arranged in at least one row in a direction in which an object under inspection enters and leaves the scanning passage.

15. The stationary CT apparatus of claim 1, wherein the plurality of detector modules are arranged in at least one row in a direction in which an object under inspection enters and leaves the scanning passage.

16. The stationary CT apparatus of claim 1, further comprising:
a correction device disposed between the plurality of ray emission focal spots and the plurality of detector modules for controlling doses of ray beams from the ray emission focal spots.

17. The stationary CT apparatus of claim 16, wherein the correction device is a grid device made of a W—Ni—Fe alloy.

18. The stationary CT apparatus of claim 17, wherein a distance between the correction device and the ray receiving surfaces of the detector modules is at least five times as large as a distance between the correction device and the ray emission focal spots.

19. The stationary CT apparatus of claim 1, wherein the X-ray source is a carbon nanotube X-ray source.

20. The stationary CT apparatus of claim 1, wherein a control of the plurality of ray emission focal spots of the X-ray source is achieved by a Controller Area Network (CAN) bus, and the ray emission focal spots may be arranged at the same intervals over a length, and a sequence in which the ray emission focal spots emit rays may be arranged along a straight line or a curve.

* * * * *